United States Patent [19]
Bouchoux et al.

[11] 3,954,738
[45] May 4, 1976

[54] STABILIZED EPSILON CAPROLACTAM COMPOSITION AND METHOD FOR PREPARING SAME

[75] Inventors: Jean W. Bouchoux, Nutley; William A. Larkin, Morristown, both of N.J.

[73] Assignee: M&T Chemicals Inc., Greenwich, Conn.

[22] Filed: Jan. 4, 1974

[21] Appl. No.: 430,690

[52] U.S. Cl. .................. 260/239.3 R; 260/239 A; 260/270 R; 260/299; 252/389 R; 252/400 R; 260/78 R
[51] Int. Cl.² .................................... C07D 223/10
[58] Field of Search .................. 252/389 R, 400 R; 260/239 A, 239.3 R, 270 R, 299

Primary Examiner—Henry R. Jiles
Assistant Examiner—Robert T. Bond
Attorney, Agent, or Firm—Robert P. Auber; Kenneth G. Wheeless; Robert Spector

[57] ABSTRACT

Hexaorgano distannanes of the general formula $R_3Sn-SnR_3$ significantly reduce or eliminate the discoloration which occurs when mixtures containing an alkali metal salt of a lactam are stored under an inert atmosphere for extended periods of time at temperatures between ambient and 100°C. R in the foregoing formula represents a monovalent hydrocarbon radical containing between 1 and 20 carbon atoms.

6 Claims, No Drawings

STABILIZED EPSILON CAPROLACTAM COMPOSITION AND METHOD FOR PREPARING SAME

BACKGROUND

This invention relates to the stabilization of salts derived from a lactam and an alkali metal.

Lactams of the general formula

are employed as starting materials for the preparation of high molecular weight polyamides. The homopolymer of ε-caprolactam is often referred to as "nylon 6". These lactam polymers exhibit excellent tensile properties and can be formed into a variety of useful products including textile denier fibers, films, castings and molded objects. Pure, dry lactams, particularly ε-caprolactam, do not polymerize appreciably even at elevated temperatures; however the polymerization can be activated using any one of a large number of materials as catalysts. Alkali metal salt of lactams are particularly effective catalysts, and are discussed by W. E. Hanford and R. M. Joyce [Journal of Polymer Science, Volume 3, No. 2, pages 167–172 (1948)]. The polymerization proceeds rapidly at temperatures between 200° and 280°C. and is conveniently carried out by adding the desired amount of alkali metal to the lactam to effect, first, salt formation, followed by a polymerization which is catalyzed by the salt. A major shortcoming of the alkali metal salts of lactams is that they discolor relatively rapidly even under inert atmospheres, particularly at the elevated temperatures employed to liquefy and polymerize lactams. The color imparted to the resultant polymer renders it unacceptable for many end uses, particularly as textile fiber and film.

It is therefore an object of the present invention to eliminate or at least significantly reduce the discoloration which occurs in compositions containing an alkali metal salt of a lactam.

A second objective of this invention is to stabilize polymerizable mixtures containing a lactam and an alkali metal salt of said lactam without adversely affecting the activity of the alkali metal salt as a latent polymerization catalyst.

It has now been found that these objectives can be attained when a hexaorgano distannane is present in combination with an alkali metal lactam salt.

SUMMARY OF THE INVENTION

The present invention provides stabilized compositions containing an alkali metal salt of a lactam, wherein said salt exhibits the general formula

and a hexaorgano distannane of the general formula $R_3{}^2Sn\text{-}SnR_3{}^3$, in an amount between 0.5 and about 100 percent, based on the weight of said salt, wherein $R^1$ represents an alkylene radical containing between 2 and 6 carbon atoms, inclusive, and M represents an alkali metal selected from the group consisting of lithium, sodium and potassium. $R^2$ and $R^3$ are individually selected from the group consisting of alkyl radicals containing between 1 and 20 carbon atoms, cycloalkyl, aralkyl, aryl and alkaryl radicals.

This invention further provides improved compositions suitable for use in preparing polyamides or polyesteramides by the catalyzed homopolymerization or copolymerization of lactams. These compositions contain one or more lactams and a catalytic amount of an alkali metal salt of a lactam, wherein the improvement resides in the presence of between 0.5 and 100 percent, based on the weight of said salt, of a hexaorgano distannane.

DETAILED DESCRIPTION OF THE INVENTION

The alkali metal lactam salts that can be stabilized against discoloration using the present hexaorgano distannanes are derived from the reaction of the corresponding alkali metals, which include lithium, sodium and potassium, with lactams i.e. cyclic amides of amino acids, containing between 3 and 7 carbon atoms. The lactams include γ-butyrolactam, δ-valerolactam and ε-caprolactam. The reaction of these lactams with an alkali metal is believed to proceed as set forth in the following equation:

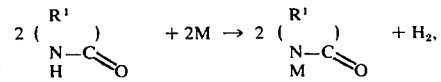

wherein $R^1$ and M are as previously defined.

The hexaorgano distannanes that prevent or inhibit discoloration of the foregoing lactam derivatives exhibit the general formula $R_3{}^2Sn\text{-}SnR_3{}^3$ wherein $R^2$ and $R^3$ each represent an alkyl radical which may contain between 1 and 20 carbon atoms, a cycloalkyl, aralkyl, alkaryl or an aryl radical. Suitable alkyl radicals include methyl, ethyl, n-propyl, iso-propyl, n-butyl, sec-butyl, tert-butyl and higher homologs containing between 5 and 20 carbon atoms. Alternatively, one of the hydrogen atoms of the alkyl radical can be replaced by an aryl radical, yielding an aralkyl radical such as benzyl or β-phenylethyl. Cycloalkyl radicals include cyclopentyl, cyclohexyl and cyclooctyl. Aryl radicals which can be represented by $R^2$ and/or $R^3$ include phenyl and naphthyl. One or more hydrogen atoms of the aryl radical can be replaced by a methyl or other alkyl radical to form an aralkyl radical such as o—, m— or p-tolyl or one of the isomeric xylyl radicals. Preferably $R^2$ and $R^3$ represent alkyl radicals containing between 1 and 4 carbon atoms. It should be pointed out that while $R^2$ and $R^3$ are preferably identical, this is not a requirement. Methods for preparing "unsymmetrical" hexaorgano distannanes are well known in the art, for example by the reactions described by W. P. Neumann et al. [Annalen der Chemie, Vol. 692, pages 1–11 (1966)].

The minimum concentration of organotin compound required to prevent or inhibit discoloration of compositions containing the alkali metal salt of a lactam depends to a large extent upon the length of time during which the composition will be stored and the temperatures to which the mixture will be exposed during processing and storage. A concentration of between 0.5 and 100 percent, based on the weight of alkali metal salt, is usually sufficient to prevent or at least significantly reduce the discoloration which occurs during formation and storage of the salt. As will be described in the examples which form part of this specification, the salts are often prepared by addition of the alkali metal to the molten lactam under an inert atmosphere such as nitrogen. The preferred lactam, $\epsilon$-caprolactam, is a solid that melts at 69°C. The amount of alkali metal added can be sufficient to react with all of the lactam present in the reaction mixture. If the resultant salt is to be employed as the catalyst for a lactam polymerization, it is common practice to employ only enough alkali metal to yield the concentration of salt required to catalyze the polymerization. The amount of catalyst usually is between 0.05 and 5 percent, based on the weight of lactam. Alternatively, a mixture of lactam and the alkali metal salt thereof can be employed as a catalyst concentrate which is subsequently combined with additional lactam prior to polymerization to achieve the desired catalyst concentration. The mixture of salt and lactam is then heated under an inert atmosphere at temperatures between 200° and 300°C. for a length of time sufficient to achieve the desired molecular weight.

The present alkali metal salts of lactams can be employed as catalysts for the copolymerization of two or more lactams or a polymerization involving one or more lactams and one or more lactones. The lactams preferably contain 5 or 7 atoms in the ring whereas the lactones contain 4, 6 or 8 atoms.

The following examples demonstrate preferred embodiments and should not be interpreted as limiting the scope of the invention defined in the appended claims.

EXAMPLE 1

The compositions employed to evaluate the stabilizers were prepared by transferring 50 cc. samples of molten $\epsilon$-caprolactam under a nitrogen atmosphere into containers which had previously been filled with nitrogen and charged with the desired amount of stabilizer. The containers were then placed in a water bath maintained at a temperature of 73±2°C. Between 0.18 and 0.20 g. of sodium metal was then placed in each of the containers. The resultant hydrogen evolution was allowed to continue for between 3 and 5 minutes, as required, at which time the containers were sealed and the temperature of the water bath raised to 80±5°C. The samples remained in the water bath for 24 hours, at which time they were removed and allowed to cool. The yellowness index of the resultant solid materials were measured using a Meeco Colormaster Differential Colorimeter manufactured by Manufacturers Engineering and Equipment Corp. This instrument measures the percent green, red and blue light which is reflected from the sample. The yellowness index (Y.I.) is calculated using the equation Y.I. = (percent red reflectance - percent blue reflectance) / percent green reflectance.

Since the discoloration of the sodium salt in almost all instances produces a shade of yellow, the yellowness index provides a suitable means for determining the stability imparted by the various compounds tested. By definition the yellowness index is directly proportional to the intensity of this color.

The yellowness index values obtained using a variety of known stabilizers, including the present hexaorgano distannanes are recorded in the following table together with the amount of stabilizer present in the test sample.

| Stabilizer | Amount (g.) | Yellowness Index | |
| --- | --- | --- | --- |
| None (control) | — | 0.385, | 0.385 (2 trials) |
| hexamethyl distannane | 0.2 | 0.160 | |
| hexamethyl distannane | 0.1 | 0.166 | |
| hexabutyl distannane | 0.2 | 0.193 | |
| hexabutyl distannane | 0.1 | 0.243 | |
| Controls (prior art stabilizers) | | | |
| butyl stannoic acid | 0.2 | 0.300 | |
| 2,4-di-t-butyl-p-cresol | 0.2 | 0.304 | |
| di-n-butyltin-S,S'-bis (lauryl mercaptide) | 0.2 | 0.308 | |
| bis(tri-n-butyltin) oxide | 0.2 | 0.335 | |
| tetrabutyltin | 0.2 | 0.359 | |
| stannous oxalate | 0.2 | 0.373 | |
| triphenyl phosphine | 0.2 | 0.384 | |
| triphenyl antimony | 0.2 | 0.466 | |

The foregoing data demonstrate that the intensity of the yellow color which develops in compositions containing the sodium salt of $\epsilon$-caprolactam and the present hexaorgano distannanes is considerably less when compared against identical compositions containing known organotin and other stabilizers, even those which the prior art discloses as being effective stabilizers for polyamides. For example, U.S. Pat. No. 3,159,575 teaches the use of alkylstannoic acids for stabilizing polyamides while U.S. Pat. No. 3,189,575 discloses that various classes of organotin compounds, including tetraorganotin compounds, organotin halides, -oxides, -sulfides and compounds containing bonds from tin to nitrogen or phosphorus are suitable for this purpose.

EXAMPLE 2

A polymer of $\epsilon$-caprolactam was prepared by adding 0.2 g. of sodium metal and 0.2 g. of hexabutyl distannane to a 50 cc. sample of $\epsilon$-caprolactam under the conditions described in Example 1. The sample was then heat treated at 80±5°C. for 24 hours. The sealed container was then placed inside a steel pipe. The pipe was sealed on both ends and then placed in a circulating air oven heated to a temperature of 250°C. for one hour. The resultant polymer was off-white in color and exhibited an inherent viscosity of 0.79 measured at 25°C. using a solution containing 0.5 percent of polymer in meta-cresol. This corresponds to a number average molecular weight of 11,000.

A mixture of $\epsilon$-caprolactam and the sodium salt thereof which did not contain any stabilizer was prepared and polymerized as described in the preceding paragraph. The polymer exhibited an inherent viscosity of 0.54, which corresponds to a number average molecular weight of 6200.

The number average molecular weight for each of the foregoing polymer samples was calculated using the formula $$\overline{M}_n = 15,600 \times (\eta_{inh})^{1.49}.$$

$\overline{M}_n$ represents the number average molecular weight and $\eta_{inh}$ the inherent viscosity.

What is claimed is:

1. An improved composition containing 1) an alkali metal salt of ε-caprolactam wherein said alkali metal is selected from the group consisting of lithium, sodium and potassium, and 2) a stabilizer to inhibit discoloration of said composition, wherein the improvement resides in the presence, as said stabilizer, of a hexaorgano distannane of the formula $R_3^2SnSnR_3^2$ in an amount between SnSnRand 100 percent, based on the weight of said alkali metal salt, wherein $R^2$ and $R^3$ each represent an alkyl radical containing from 1 to 20 carbon atoms, inclusive.

2. The improved composition of claim 1 wherein the composition contains ε-caprolactam and a catalytic amount of said alkali metal salt sufficient to promote the polymerization of the lactam.

3. The improved composition of claim 1 wherein the alkali metal is sodium.

4. A method for preventing or inhibiting the development of discoloration in compositions containing an alkali metal salt of ε-caprolactam, said method consisting of incorporating into said composition between 0.5 and 100 percent, based on the weight of said alkali metal salt, of a hexaorgano distannane of the general formula $R_3^2SnSnR_3^3$ wherein $R^2$ and $R^3$ each represent an alkyl radical containing from 1 to 20 carbon atoms, inclusive.

5. The method of claim 4 wherein the composition contains ε-caprolactam and a catalytic amount of said alkali metal salt sufficient to promote the polymerization of the lactam.

6. The method of claim 4 wherein the alkali metal is sodium.

\* \* \* \* \*

UNITED STATES PATENT OFFICE
CERTIFICATE OF CORRECTION

Patent No. 3,954,738            Dated May 4, 1976

Inventor(s) Jean W. Bouchoux et al.

It is certified that error appears in the above-identified patent and that said Letters Patent are hereby corrected as shown below:

Claim 1, line 8 - Delete "SnSnR" and substitute therefor --0.5--.

Signed and Sealed this

Twenty-seventh Day of July 1976

[SEAL]

Attest:

RUTH C. MASON
*Attesting Officer*

C. MARSHALL DANN
*Commissioner of Patents and Trademarks*